United States Patent
Azria et al.

(10) Patent No.: US 8,323,688 B2
(45) Date of Patent: Dec. 4, 2012

(54) PHARMACEUTICAL COMPOSITIONS COMPRISING HGH FOR ORAL DELIVERY

(75) Inventors: Moise Azria, Basel (CH); Yatindra Joshi, Princeton, NJ (US); Rosario Lobrutto, Highland Mills, NY (US); Linda Mindeholm, Bettlach (FR); Ashish B Patel, West Orange, NJ (US)

(73) Assignee: Novartis AG, Basel (CH)

( * ) Notice: Subject to any disclaimer, the term of this patent is extended or adjusted under 35 U.S.C. 154(b) by 334 days.

(21) Appl. No.: 12/377,401

(22) PCT Filed: Aug. 28, 2007

(86) PCT No.: PCT/US2007/076932
§ 371 (c)(1),
(2), (4) Date: Feb. 13, 2009

(87) PCT Pub. No.: WO2008/027854
PCT Pub. Date: Mar. 6, 2008

(65) Prior Publication Data
US 2010/0247608 A1   Sep. 30, 2010

Related U.S. Application Data

(60) Provisional application No. 60/824,140, filed on Aug. 31, 2006.

(51) Int. Cl.
*A61K 38/27* (2006.01)
*A61K 9/20* (2006.01)
*A61P 5/06* (2006.01)
*C07C 229/00* (2006.01)

(52) U.S. Cl. .................. 424/464; 514/11.4; 562/444

(58) Field of Classification Search .............. None
See application file for complete search history.

(56) References Cited

U.S. PATENT DOCUMENTS

| 5,350,741 A | * | 9/1994 | Takada ........................ 424/85.2 |
| 5,773,647 A | * | 6/1998 | Leone-Bay et al. .......... 562/444 |
| 2002/0123459 A1 | * | 9/2002 | Ault et al. ...................... 514/2 |
| 2008/0207513 A1 | * | 8/2008 | Liu et al. ....................... 514/12 |

FOREIGN PATENT DOCUMENTS

| WO | WO 98/34632 | 8/1998 |
| WO | WO 00/59863 | 10/2000 |
| WO | WO 02/45754 | 6/2002 |
| WO | 2005/004900 | 1/2005 |
| WO | 2007/035718 | 3/2007 |

OTHER PUBLICATIONS

CAS (STN) Registry No. 204852-67-5 (published Apr. 30, 1998).*
Liao et al. Protective mechanism of stabilizing excipients against dehydration in the freeze-drying of proteins. Pharm. Res. Dec. 2002;19(12):1854-61.*
CAS (Chemical Abstracts Service) Registry No. 204852-67-5 (published Apr. 30, 1998).*

* cited by examiner

*Primary Examiner* — Daniel Sullivan
*Assistant Examiner* — Peter Anthopolos
(74) *Attorney, Agent, or Firm* — Ann R. Pokalsky, Esq.; Dilworth & Barrese, LLP

(57) ABSTRACT

The present invention relates to dosage forms of human growth hormone, the use of an absorption enhancer to allow absorption of human growth hormone into the systemic circulation in a biologically active form, in particular after oral administration, as well as the use of oral dosage forms comprising human growth hormone and an absorption enhancer for the treatment of human growth hormone deficiencies and disorders associated therewith.

14 Claims, No Drawings

PHARMACEUTICAL COMPOSITIONS COMPRISING HGH FOR ORAL DELIVERY

This application is a 371 of PCT/US2007/76932 filed on Aug. 28, 2007, which claims benefit of U.S. Provisional Application No. 60/824,140, filed Aug. 31, 2006, which in their entirety are herein incorporated by reference.

BACKGROUND OF THE INVENTION

Growth hormone (GH) is a polypeptide hormone normally synthesized and secreted by the somatotrophic cells of the anterior lobe of the pituitary gland. The secretion of GH is tightly regulated by an integrated system of neural, metabolic and hormonal factors. Although GH is present throughout life, its secretion is both age- and sex-dependent.

GH binds to specific receptors on hepatocytes, fibroblasts and lymphoid cells. The known physiological roles of GH are probably due to both direct actions and indirect actions that are mediated by insulin-like growth factors, IGFs. IGFs are themselves peptide hormones, whose secretion is stimulated predominantly by the action of GH, and include IGF-I and IGF II. The major site of IGF production is the liver, but there may also be synthesis at peripheral sites.

GH has profound effects not only on growth, but also on body composition and metabolism. Via the IGFs, GH increases protein synthesis by enhancing amino acid uptake and directly accelerating the transcription and translation of mRNA. In addition, GH tends to decrease protein catabolism by mobilizing fat as a more efficient fuel source. This protein sparing effect may be the most important mechanism by which GH promotes growth and development. GH also affects carbohydrate metabolism. There are suggestions that short-term constant infusion of GH has insulin-like effects, whereas GH in excess decreases carbohydrate utilization and impairs glucose uptake into cells, showing an anti-insulin effect. This GH-induced insulin resistance appears to be due to a post-receptor impairment in insulin action and results in glucose intolerance that in turn stimulates insulin secretion. In normal development, GH and IGFs are responsible for many of the manifestations of normal growth. Growth hormone deficiency (GHD) is manifested by a marked short stature.

The treatment of GHD began in 1958. Due to the species specificity of GH, treatment can only be performed by using human growth hormone (hGH), which at that time could only be obtained by purifying pituitary glands collected at necropsy. Because of the limited number of pituitary glands available, a world-wide shortage of hGH occurred and its use was restricted to severely growth retarded children with GHD. Recombinant DNA technology made it possible to produce a biosynthetic GH identical to hGH. Clinical studies of recombinant hGH (r-hGH) began in 1981 and the response of children with GHD to r-hGH therapy has been well documented. Moreover, the production of r-hGH has allowed further investigation of the anabolic potential of this compound. Recent studies with r-hGH have shown that supraphysiological doses promote positive nitrogen balance, improve body protein homeostasis under catabolic conditions, and may accelerate recovery during critical illness in many groups of subjects.

Subcutaneous (s.c.) hGH administration is occasionally hampered by administration difficulties and local irritation. The continuous use of s.c. hGH in children is particularly problematic. An oral form of hGH would improve patient acceptance and facilitate improved patient compliance by providing a more acceptable delivery route for peptide therapy.

There have been many attempts to promote absorption of poly (amino acids) such as peptide and proteins, e.g. hormones. It is generally believed that peptides and proteins need to be protected from the gastric and intestinal environment, where many peptidases exist and significant degradation may occur. Enteric coating and the addition of peptidase inhibitors to pharmaceutical compositions have proven to be effective in improving poly(amino acid), e.g. protein and peptide, absorption via oral administration. However, those approaches alone do not offer sufficient protection to achieve a satisfactory plasma level of a peptide or a protein, such as human growth hormone.

Carrier compounds and compositions which are useful in the delivery of active agents have been suggested, among other things for delivering peptide or protein active agents. WO 98/34632 A1 discloses amino acid derivatives as carrier compounds which are suited to form non-covalent mixtures with biologically-active agents. Among the compounds is 8-(N-2 hydroxy-5-chlorobenzyl)aminocaprylic acid (compound #109). This compound may also be referred to as N-(5-chlorosalicyloyl)-8-aminocaprylic acid and will herein be abbreviated as 5CNAC.

WO 98/34632 A1 furthermore discloses solutions containing a carrier compound and recombinant human growth hormone (Example 4). Several carriers are investigated, among them 5-CNAC (i.e. 8-(N-2-hydroxy-5-chlorobenzyl)aminocaprylic acid, compound #109). The compound is contained in an intracolonic dosing composition in a weight ratio of carrier to growth hormone of 25:1. The intracolonic dosing composition is administered to anaesthetised rats by intracolonic instillation (Example 5), and the serum level of human growth hormone after administration is determined.

For some other carriers, WO 98/34632 A1 describes oral solutions having a weight ratio of carrier to growth hormone of 200:1 that are also tested in rats.

WO 98/34632 A1 contains no data relating to administration of growth hormone to humans and also contains no evidence for biological activity of the administered growth hormone. There is no disclosure of a solid oral dosage form, such as a capsule or a tablet.

WO 00/59863 A1 discloses disodium salts, monohydrates and ethanol solvates of certain delivery agents, among them N-(5-chlorosalicyloyl)-8-aminocaprylic acid (5-CNAC).

WO 00/59863 A1 also suggests compositions containing various active agents. Human growth hormone is mentioned in a long list of active agents, but there is no growth hormone formulation examplified, and there are no data regarding the administration of any growth hormone formulation. For a composition containing a preferred active agent according to WO 00/59863 A1, namely calcitonin. weight ratios of active agent to 5-CNAC of about 1:300 to 1:700 are suggested (WO 00/59863 A1, page 8).

WO 2005/004900 A1 describes orally dosed pharmaceutical compositions comprising a delivery agent in micronized form. 5-CNAC is among the delivery agents mentioned. WO 2005/004900 A1 furthermore mentions growth hormone as an active agent, but there are no details disclosed for the specific combination, and there are also no data relating to the administration of growth hormone to patients. The only exemplified formulation comprises salmon calcitonin and 5-CNAC in a weight ratio of 1:228.

While the prior art suggests in general terms to combine active agents such as hGH with a carrier compound, such as 5-CNAC, there are no data that would demonstrate that an hGH oral dosage form shows biological effects, such as stimulation of IGF production. Furthermore, the prior art seems to indicate that a significant excess of carrier compound relative to biologically active ingredient, such as human growth hormone, is needed for absorption. Nevertheless, it remains unclear whether the absorbed material shows the biological activities of human growth hormone, such as stimulation of an IGF-I response.

Despite the above suggestions regarding delivery of peptide and protein active agents, hGH is currently still administered by injection. There exists a long-felt need for an oral dosage form, in particular a solid oral dosage form, such as a capsule or tablet.

Thus, it is an object of the present invention to provide pharmaceutical compositions useful for the oral administration of hGH.

Furthermore, it may be advantageous to use relatively small amounts of carrier or delivery agent in relation to the active agent, in particular for dosage forms containing human growth hormone in a therapeutically effective amount of, for instance in the order of 100 mg, as such dosage forms would have advantages in administration, e.g. would be easier for a patient to swallow.

Thus, it is a further object of the invention to provide useful solid oral dosage forms which contain therapeutically effective amounts of human growth hormone.

Although 5-CNAC is generally well-tolerated, there is a desire to avoid exposure to excessive amounts of the agent, in particular during long-term administration.

Thus, it is a still further object of the invention to provide dosage forms of human growth hormone which are suitable for oral delivery of the active agent, but which avoid the exposure of the patient to large amounts of delivery agents, such as 5-CNAC.

SUMMARY OF THE INVENTION

The present invention therefore provides a pharmaceutical composition that enables the successful delivery of human growth hormone (hGH), to a subject via oral administration.

In particular, the present invention provides pharmaceutical compositions comprising a human growth hormone as the active ingredient together with the delivery agent 5-CNAC, where the pharmaceutical provides oral bioavailability, e.g. satisfactory or optimal oral bioavailability for the human growth hormone active ingredient.

In one aspect, the present invention further provides a pharmaceutical composition comprising human growth hormone (hGH) and N-(5-chlorosalicyloyl)-8-aminocaprylic acid (5-CNAC), optionally in the form of a pharmaceutically acceptable salt and/or solvate, in a weight ratio of hGH to 5-CNAC from 1:0.2 to 1:50, calculated on the basis of 5-CNAC in the free acid form.

The human growth hormone containing pharmaceutical compositions of the present invention may be used to treat disorders related to a growth hormone deficiency as well as conditions where supraphysiological hGH levels can be beneficial.

DETAILED DESCRIPTION OF THE INVENTION

Human Growth Hormone

Human Growth Hormone (hGH) (or somatotropic hormone or somatotropin) is a polypeptide hormone secreted by the anterior lobe of the pituitary gland that promotes growth of the body, especially by stimulating release of somatomedin, and that influences the metabolism of proteins, carbohydrates, and lipids.

Included under the hGH definition may also be any of various natural or synthetic substances that regulate the growth of animals or plants, such as pituitary growth hormone in vertebrates and auxins in plants. More in particular, as used herein, the terms "human growth hormone" or "hGH" denote human growth hormone produced by methods including natural source extraction and purification, and by recombinant cell culture systems. The sequence and characteristics of hGH are described, for example, in Hormone Drugs, Gueriguian et al., U.S.P. Convention, Rockville, Md. (1982).

The terms "human growth hormone" or "hGH" are intended to also include biologically active human growth hormone equivalents, e.g., differing in one or more amino acid(s) in the overall sequence. Furthermore, the terms are intended to cover substitution, deletion and insertion amino acid variants of hGH, or posttranslational modifications. Two well-known species are the 191 amino acid native species (somatropin) and the 192 amino acid N-terminal methionine (met) species (somatrem) commonly obtained by recombinant methods. The 191 amino acids form having the native sequence (somatropin) is the preferred form of hGH according to the present invention. This means that for all compositions disclosed herein it is preferred that they contain somatropin.

A further preferred form of human growth hormone is a polymer-modified hGH, for instance a polymer-modified somatropin. By "polymer-modified" it is meant that one or more polymer chains are covalently attached to the hGH molecule, for instance the somatropin molecule. Several polymers have been suggested for polymer-modification of proteins, in particular water-soluble polymers. PEG (polyethylene glycol) is one of the most often used polymer for protein modification, and pegylated forms of human growth hormone, for instance pegylated forms of somatropin, are considered to be particularly useful. Properties as well as preparation methods for pegylated active agents including proteins such as hGH have been reviewed by G. Pasut et al. in Expert. Opin. Ther. Patents (2004) 14(6) pp. 859-894. The contents of this review are incorporated herein by reference.

For all compositions disclosed herein, the use of polymer-modified hGH as discussed above, in particular of pegylated hGH, such as pegylated somatropin, constitutes a preferred embodiment.

Human growth hormone can be employed in lyophilized form. Lyophilisation of hGH is known in the art. Reference may be made to M. Pikal et al.: Pharmaceutical Research, vol. 8, no. 4, 1991, pp. 427-436 and to M. Pikal et al.: Develop. Biol. Standard, vol. 74, 1991, pp. 21-38. The contents of both publications are incorporated herein by reference.

Delivery Agent

Pharmaceutical compositions according to the present invention contain 5-CNAC as a delivery agent. 5-CNAC is used herein as an abbreviation for N-(5-chlorosalicyloyl)-8-aminocaprylic acid. The compound is also known as 8-(N-2-hydroxy-5-chlorobenzyl) aminocaprylic acid.

5-CNAC is a known compound. The compound is for instance disclosed in WO 98/34632 A1 (8-(N-2-hydroxy-5-chlorobenzyl)aminocaprylic acid, compound #109).

5-CNAC can be prepared according to known methods. Reference is again made to WO 98/34632 A1. The contents of this application are hereby incorporated by reference in their entirety.

Further information regarding delivery agents and their preparation may be found in U.S. Pat. Nos. 5,773,647 and 5,866,536, the contents of which are hereby incorporated by reference in their entirety.

5-CNAC will usually be used in the compositions of the present invention in the form of a pharmaceutically acceptable salt and/or solvate, i.e. a salt, a solvate of the free acid or a solvate of a salt. These forms of 5-CNAC include the mono and di-salts, for example monosodium and disodium salts, ethanol solvates of the salts and monohydrates of the salts and any combinations thereof, such as ethanol solvates of the sodium salts and monohydrates of the sodium salts. Other salts with pharmaceutically acceptable cationic moieties, such as potassium, lithium and calcium, are also contemplated. Preferably, the 5CNAC salt comprises a divalent cationic moiety and a divalent 5-CNAC anionic moiety.

In especially preferred embodiments, the delivery agent is the disodium salt of 5-CNAC (5CNAC dss), possibly in the form of a solvate or hydrate thereof. This means that for all compositions disclosed herein it is preferred that they contain 5-CNAC dss.

The form of the 5-CNAC dss is not limited and includes all pharmaceutically acceptable solvates and hydrates, in particular the monohydrate as well as hydrates having different water content. Furthermore all solid forms, for instance all crystal forms, of 5-CNAC dss and of its solvates or hydrates may be used.

With respect to salts and/or solvates of 5-CNAC as discussed above, in particular the disodium salt, and their preparation, reference is made to WO 00/59863 A1, the contents of which are hereby incorporated by reference in their entirety.

5-CNAC and particular the forms of 5-CNAC as discussed above, such as the salts, including the disodium salt, can be used in micronised form in the pharmaceutical compositions according to the present invention.

In a particularly preferred class of pharmaceutical compositions, the delivery agent is 5CNAC. The 5-CNAC may be in free or salt form and may consist of a wide range of particle sizes ranging from, for example, 50 to 5 μm average particle size. Preferably, the delivery agent is in micronised form. The average particle size of the micronised delivery agent, e.g. 5-CNAC, may be measured by milling coarse 5-CNAC and sampling periodically with reference particle size measurements to identify when the averaged desired particle size is achieved. A process for micronising 5-CNAC is described in WO 2005/014031, which is incorporated herein by reference; see in particular page 10 and example 1, which describe the effects of different 5CNAC size particles.

Pharmaceutical Compositions

The pharmaceutical compositions of the present invention may be provided as a capsule including a soft-gel capsule, tablet, caplet or other solid oral dosage form, all of which can be prepared by methods well known in the art. Capsules and in particular tablets are preferred.

According to one aspect of the invention, there is provided a pharmaceutical composition comprising human growth hormone (hGH) and N-(5-chlorosalicyloyl)-8-aminocaprylic acid (5-CNAC), optionally in the form of a pharmaceutically acceptable salt and/or solvate, in a weight ratio of hGH to 5-CNAC from 1:0.2 to 1:50, calculated on the basis of 5-CNAC in the free acid form. Preferably, the weight ratio as defined is in the range of 1:0.2 to 1:50, more in particular in the range of 1:0.2 to 40. More preferred ranges are 1:0.5 to 1:10, even more preferred 1:0.5 to 1:5. The most preferred ratio is about 1:2.

The absolute amount (weight) of the growth hormone in the present compositions depends on a number of factors well known to those skilled in the art. The amount of pharmacologically active agent is generally an amount effective to accomplish the intended purpose, e.g. a therapeutically effective amount.

Typically, a pharmaceutical composition according to the present invention, as a unit dosage form, comprises an amount of hGH is in the range of 10 to 300 mg, preferably in the range of 50 to 200 mg. A preferred amount of hGH is about 100 mg.

The pharmaceutical compositions of the present invention, in unit dosage form, typically comprise 5-CNAC (optionally in the form of a pharmaceutically acceptable salt and/or solvate) in an amount in the range of 50 to 400 mg, preferably in the range of 100 to 300 mg, calculated on the basis of 5-CNAC in the free acid form. A preferred amount of 5-CNAC is about 200 mg, calculated on the basis of 5-CNAC in the free acid form.

Suitable amounts of hGH and/or 5-CNAC can for instance be determined by comparing the plasma levels obtained after administration of pharmaceutical compositions of the present invention with those achieved after administration of known injectable forms, such a commercially available hGH injection formulations, taken recommended dosing into consideration.

The total weight of a unit dosage form, such as a capsule or tablet, is in general not more than 1600 mg, preferably not more than 1200 mg, in particular not more than 1000 mg and still further preferably not more than 800 mg.

A pharmaceutical composition according to the present invention typically contains one or more pharmaceutically acceptable excipients in addition to hGH and 5-CNAC. These excipients are conventional and typically include a disintegrant, a diluent, a glidant, and/or a lubricant.

The compositions may additionally comprise additives in amounts customarily employed including, but not limited to, a pH adjuster, a preservative, a flavorant, a taste-masking agent, a fragrance, a humectant, a tonicifier, a colorant, a surfactant, a plasticizer, a solubilizer, or any combination thereof. Other additives may include phosphate buffer salts, citric acid, glycols, and other dispersing agents.

In a preferred embodiment of the present invention, the diluent is a microcrystalline cellulose, e.g. Avicel PH 101® (supplied by FMC corporation 1735 Market Street Philadelphia, Pa. 19103, USA).

Also in a preferred embodiment of the present invention, the lubricant is magnesium stearate.

The disintegrant may preferably be selected from any superdisintegrant, of which crospovidones and povidones may be mentioned in particular. Crospovidone is a synthetic crosslinked homopolymer of N-vinyl-2-pyrrolidone. Commercially available crospovidones include Polyplasdone XL available from ISP.

In a preferred embodiment of the invention, the pharmaceutical composition comprises microcrystalline cellulose, crospovidone and magnesium stearate, besides hGH, especially in lyophilised form, and 5-CNAC, especially in the form of its disodium salt.

Pharmaceutical compositions according to the present invention can be prepared in a conventional manner.

Solid pharmaceutical compositions may be prepared by first grinding the ingredients of the present composition, if desired to a micronized particle size. The ingredients may then be further processed by conventional methods e.g. by blending a mixture of the active agent, the delivery agent, and other ingredients, kneading, and filling into capsules or, instead of filling into capsules, molding followed by further tableting or compression-molding to give tablets.

According to the present invention, solid oral dosage forms can also be provided in the form of a powder or granulate. A suspension, which for instance can be prepared form such a powder or granulate, also forms part of the present invention.

Solid oral doses forms of the present invention preferably have an enteric coating. Enteric coatings are known in the art. Some of the known enteric coatings are based on acrylic resins which are commercially available in the form of various Eudragit brands (trademark of Röhm Pharma Polymers). Such known coatings may be used. There are also conventional tests available that allow determining whether any dosage form is resistant to gastric juice but dissolves upon entering the intestine. Test as defined for instance in the US Pharmacopoeia may be employed. Sustained release formulations for the pharmaceutical compositions of the invention are also preferred, and formulations using OROS® or hydroxypropyl methylcellulose (HPMC) are particularly suitable for use according to the invention.

According to one embodiment, the pharmaceutical composition of the present invention is provided in the form of a suppository. The suppository contains human growth hormone and 5-CNAC as discussed above. Furthermore, the suppository contains ingredients of suppositories as are well known in the art. These include PEGs, fats, such as adeps, neutralis, cocoa butter, cetyl alcohol, glycerides of fatty acids, cutina and the like. Protease inhibitors may also be contained.

Methods for preparing suppositories are known in the art, and these methods can be employed for the preparation of the suppositories of the present invention.

Uses and Methods of Treatment

Pharmaceutical compositions according to the present invention may be used for the treatment of hGH deficiency. Thus, the present invention includes a method of treatment by administering to a patient in need thereof a therapeutically effective dose of a pharmaceutical composition as defined herein. The administration is in particular an oral administration of an oral dosage form according to the invention. The patients treated are in particular growth retarded children.

The invention is furthermore directed to the use of hGH for the preparation of a pharmaceutical composition as defined herein for the treatment of hGH deficiency, for instance in growth retarded children.

Pharmaceutical compositions according to the present invention may also be used for the treatment, of patients suffering from Turner syndrome. Thus, the present invention includes a method of treatment by administering to a patient in need thereof, who suffers from Turner syndrome, a therapeutically effective dose of a pharmaceutical composition as defined herein. The administration is in particular an oral administration of an oral dosage form according to the invention.

The invention is furthermore directed to the use of hGH for the preparation of a pharmaceutical composition as defined herein for the treatment of Turner syndrome.

Still further, pharmaceutical compositions according to the present invention may be used for the treatment of patients in whom it is desired to elucidate an IGF-I response. Thus, the present invention includes a method of treatment by administering to a patient in need thereof, in particular a patient in whom it is desired to elucidate an IGF-I response, a therapeutically effective dose of a pharmaceutical composition as defined herein. The administration is in particular an oral administration of an oral dosage form according to the invention.

The invention is furthermore directed to the use of hGH for the preparation of a pharmaceutical composition as defined herein for elucidating an IGF-I response by administration of the composition.

Pharmaceutical compositions according to the present invention may also be used for the treatment of patients in whom it is desired to achieve supraphysiological hGH levels. Thus, the present invention includes a method of treatment by administering to a patient in need thereof, in particular a patient in whom it is desired to achieve supraphysiological hGH levels, a therapeutically effective dose of a pharmaceutical composition as defined herein. The administration is in particular an oral administration of an oral dosage form according to the invention.

The invention is furthermore directed to the use of hGH for the preparation of a pharmaceutical composition as defined herein for achieving supraphysiological hGH levels in a patient in need of such a treatment.

Pharmaceutical compositions according to the present invention may moreover be used for the treatment of patients in whom it is desired to promote positive nitrogen balance and/or improve body protein homeostasis under catabolic conditions, and/or accelerate recovery during critical illness. Thus, the present invention includes a method of treatment by administering to a patient in need thereof, in particular a patient in whom it is desired to promote positive nitrogen balance and/or improve body protein homeostasis under catabolic conditions, and/or accelerate recovery during critical illness, a therapeutically effective dose of a pharmaceutical composition as defined herein. The administration is in particular an oral administration of an oral dosage form according to the invention.

The invention is furthermore directed to the use of hGH for the preparation of a pharmaceutical composition as defined herein for promoting positive nitrogen balance and/or improving body protein homeostasis under catabolic conditions, and/or accelerating recovery during critical illness.

The appropriate dosage will, of course, vary depending upon, for example, the host and the nature and severity of the condition being treated. The particular dosage administered, which is efficacious and well tolerated, i.e. safe for a patient to take, will be determined by the physician. The total daily dose, which may be administered in the form of divided doses, will often be in the range of 10 to 2000 mg hGH when pharmaceutical compositions according to the present invention are administered orally.

EXAMPLES

The following examples serve to further illustrate the invention and will be readily understood by one of ordinary skill in the art. The examples are not meant to be limiting of the present invention in any way.

Example 1

Pharmaceutical Composition

The example relates to an immediate release tablet containing an hGH lyophilisate. The lyophilisate contains hGH (Somatropin):mannitol:glycine:disodium hydrogen phosphate:sodium dihydrogen phosphate in a weight ratio of 1:2:1:0.3:0.1.

For the preparation of the pharmaceutical composition, the following ingredients were used in the stated amounts:

| Ingredient | Amount (mg) |
| --- | --- |
| hGH lyo | 440 |
| 5-CNAC dss | 228 |
| Microcystalline Cellulose (Avicel PH 101) | 80 |
| Crospovidone XL | 40 |
| Magnesium stearate | 12 |
| Total | 800 |

The ingredients were processed according to a conventional method. The final blend was compressed into an 800 mg tablet.

Example 2

Clinical Study

This was a phase I single arm study carried out in growth hormone deficient adult men who were on hGH treatment. Standard hGH treatment was temporarily halted during the 2 week duration of the trial. There was a wash-out period of one week followed by one week of treatment. All patients received four tablets per day of Somatropin 100 mg during 7 days (one tablet in the morning, one tablet in the evening and two tablets at bedtime). Patients attended the centre on 3 occasions, during which they stayed once for 48 hours and once for 24 hours. Patients were allowed to split Visit 2 and 3 (48 hours) into 2 separate visits each of 24 hours. Patients were required to stop their r-hGH treatment for the duration of the trial, starting 7 days before Visit 2. If Visit 2 and 3 were split, patients continued without the normal r-hGH treatment. There was no more than 3 days between Visits 2 and 3.

Patient characteristics are summarised in the table below.

| | Patients N = 8 |
| --- | --- |
| Age (years) | |
| Mean (SD) | 48.8 (8.41) |
| Median (Range) | 50.5 (36-59) |
| Sex | |
| Male | 8 (100%) |
| Race | |
| Caucasian | 8 (100%) |
| Weight (kg) | |
| Mean (SD) | 96.43 (17.68) |
| Median (Range) | 92.70 (74.4-133.5) |

SD = standard deviation

Assessments included the evaluation of pharmacokinetic and pharmacodynamic response to Somatropin as measured by serum hGH and serum IGF-I.

Results obtained for the serum hGH pharmacokinetics (serum hGH $AUC_{0-t}$ and Cmax values) are shown as geometric mean of the values obtained for the 8 individual patients.

| | Geometric Mean | | | | | |
| --- | --- | --- | --- | --- | --- | --- |
| | Wash-out Day 7 | | Treatment Day 1 | | Treatment Day 7 | |
| | $AUC_{0-t}$ | Cmax | $AUC_{0-t}$ | Cmax | $AUC_{0-t}$ | Cmax |
| Morning | 0.01 | 0.55 | 1.38 | 2.17 | 0.75 | 1.32 |
| Evening | 0.00 | 0.28 | 0.04 | 0.64 | 0.01 | 0.49 |
| Bedtime | 0.03 | 0.43 | 2.00 | 2.80 | 0.51 | 1.09 |

$AUC_{0-t}$ is in mcgs x h/L and $C_{max}$ in microgram/L.

Five patients had higher $AUC_{0-12}$ values and four had higher Cmax values for serum hGH measured after the last dose taken in the evening of day 7 of the treatment period compared to day 7 of the wash-out period. From the individual patient hGH concentration profiles it is clear that Somatropin was rapidly absorbed and excreted, usually within 2 hours, in the majority of patients. Systemic levels of hGH were generally higher on day 1 of the treatment period compared to day 7 of the treatment period. Systemic levels of hGh were generally lower after the evening dose compared of the morning and bedtime doses.

On treatment day 7 IGF-I levels had increased from a pre-dose morning value of 135.8 µg/L on treatment day 1 to 146.3 µg/L, increasing to a value of 160.8 µg/L before the evening dose and to 150 µg/L before the bedtime dose. There was considerable variation between patients in the levels of IGF-I. Subjects 1, 3, 4, 5 and 6 had an increase from wash-out for the majority of measurements on day 7. Subjects 2 and 8 had mainly decreases in IGF-I levels over the measurement period. Subject 7 had an increase in IGF-I values on approximately half of the time-points and decreases in IGF-I for the remaining time-points. These 3 patients all had relevant endogenous hGH peaks.

The study showed that Somatropin was rapidly absorbed and rapidly excreted, normally within 2 hours, in the majority of patients. In general systemic level of Somatropin was greater on day 1 of the treatment period compared to day 7 of the treatment period. In the majority of patients, systemic levels of Somatropin were lower after the evening dose compared to the morning and bedtime doses. Following treatment with Somatropin there was a statistically significant increase in IGF-I levels on treatment day 7 when compared with values at the end of a 7 day wash-out period. The patients who had the IGF-I responses were those that had no endogenous GH secretion and/or had the highest systemic levels. Somatropin was well-tolerated and the study did not raise any specific safety concerns although it included only 8 patients.

The invention claimed is:

1. A pharmaceutical composition in solid oral dosage form comprising human growth hormone (hGH) and N(5-chlorosalicyloyl)-8-aminocaprylic acid (5-CNAC), in a weight ratio of hGH to 5CNAC of about 1:2, calculated on the basis of 5-CNAC in the free acid form, wherein the hGH is present in lyophilised form and in an amount of about 10 to 300 mg.

2. The pharmaceutical composition according to claim 1, wherein the hGH present comprises 191 amino acids and has the amino acid sequence of native human growth hormone.

3. The pharmaceutical composition according to claim 1, wherein 5-CNAC is present in the form of a salt.

4. The pharmaceutical composition according to claim 3 wherein the 5-CNAC salt comprises a divalent cationic moiety and a divalent 5-CNAC anionic moiety.

5. The pharmaceutical composition according to claim 4 wherein the 5-CNAC salt is the disodium salt (5-CNAC dss).

6. The pharmaceutical composition according to claim 1, wherein 5-CNAC is present in micronized form.

7. The pharmaceutical composition according to claim 1, wherein the amount of hGH is about 100 mg.

8. The pharmaceutical composition according to claim 1, wherein the amount of 5-CNAC is from about 50 to 400 mg calculated on the basis of 5-CNAC in the free acid form and wherein the pharmaceutical composition further comprises one or more pharmaceutically acceptable excipients.

9. The pharmaceutical composition according to claim 1, wherein the amount of 5-CNAC is about 200 mg, calculated on the basis of 5-CNAC in the free acid form.

10. The pharmaceutical composition according to claim 1, wherein the dosage form is a capsule.

11. The pharmaceutical composition according to claim 1, wherein the dosage form is a tablet.

12. The pharmaceutical composition according to claim 1, wherein the dosage form is provided with an enteric coating.

13. A method of treating an hGH deficiency, comprising administering to a patient in need thereof a pharmaceutical composition according to claim 1.

14. A method of treating an hGH deficiency, comprising administering to a patient in need thereof a pharmaceutical composition according to claim 5.

* * * * *